(12) United States Patent
Fujita et al.

(10) Patent No.: US 9,121,819 B2
(45) Date of Patent: Sep. 1, 2015

(54) GAS SENSOR

(71) Applicant: NGK Insulators, Ltd., Nagoya (JP)

(72) Inventors: Hiroki Fujita, Kasugai (JP); Sumiko Horisaka, Nagoya (JP); Mika Murakami, Nagoya (JP); Takashi Ito, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 13/860,038

(22) Filed: Apr. 10, 2013

(65) Prior Publication Data
US 2013/0220808 A1 Aug. 29, 2013

Related U.S. Application Data

(63) Continuation of application No. 13/043,888, filed on Mar. 9, 2011, now abandoned.

(30) Foreign Application Priority Data

Mar. 18, 2010 (JP) .................................. 2010-062728

(51) Int. Cl.
*G01N 27/41* (2006.01)
*G01N 27/419* (2006.01)
(Continued)

(52) U.S. Cl.
CPC .............. *G01N 27/41* (2013.01); *G01N 27/417* (2013.01); *G01N 27/419* (2013.01); *G01N 27/4071* (2013.01); *G01N 27/4074* (2013.01)

(58) Field of Classification Search
CPC ............ G01N 27/406; G01N 27/4062; G01N 27/407–27/4078; G01N 27/409; G01N 27/41; G01N 27/417; G01N 27/419

USPC ......... 204/421, 424, 423, 425, 426, 428, 431, 204/430; 205/781–785.5
See application file for complete search history.

(56) References Cited

U.S. PATENT DOCUMENTS 4,836,906 A 6/1989 Yamada et al.
5,672,811 A 9/1997 Kato et al.
(Continued)

FOREIGN PATENT DOCUMENTS

EP 2 058 653 A1 5/2009
EP 2 107 368 A2 10/2009
(Continued)

OTHER PUBLICATIONS

Japanese Office Action dated Feb. 19, 2013.

*Primary Examiner* — J. Christopher Ball
(74) *Attorney, Agent, or Firm* — Burr & Brown, PLLC (57) ABSTRACT

A gas sensor including an internal space, a first electrode, a second electrode, a pumping cell, a third electrode, a fourth electrode, a measuring cell, and a porous diffusion layer. The first and third electrodes, and the second and fourth electrodes are formed inside and outside the internal space, respectively. The pumping cell includes the first and second electrodes, and the measuring cell includes the third and fourth electrodes. The pumping cell pumps oxygen from the internal space when a predetermined voltage is applied between the first and second electrodes. The third electrode reduces an oxide gas component in a predetermined gas component to which a predetermined diffusion resistance has been applied by the porous diffusion layer. The measuring cell measures current flow between the third and fourth electrodes when a voltage corresponding to the degree of reduction in the third electrode is applied between the third and fourth electrodes.

6 Claims, 4 Drawing Sheets

(51) Int. Cl.
*G01N 27/417* (2006.01)
*G01N 27/407* (2006.01)

(56) References Cited

U.S. PATENT DOCUMENTS

| | | |
|---|---|---|
| 6,284,112 B1 | 9/2001 | Kato et al. |
| 7,153,402 B2 | 12/2006 | Nakagaki et al. |
| 7,180,596 B2 | 2/2007 | Haraguchi et al. |
| 7,704,358 B2 | 4/2010 | Ichiyanagi et al. |
| 2001/0000598 A1 | 5/2001 | Miyata et al. |
| 2004/0159547 A1 | 8/2004 | Haraguchi et al. |
| 2005/0077177 A1 | 4/2005 | Sakayanagi |
| 2005/0211554 A1 | 9/2005 | Kurachi et al. |
| 2005/0263396 A1 | 12/2005 | Naito et al. |
| 2005/0274615 A1* | 12/2005 | Naito et al. .............. 204/424 |
| 2009/0120791 A1 | 5/2009 | Miyashita et al. |
| 2009/0188620 A1 | 7/2009 | Okuda et al. |

FOREIGN PATENT DOCUMENTS

| | | |
|---|---|---|
| JP | 63-167260 A1 | 7/1988 |
| JP | 11-237362 | 8/1999 |
| JP | 2003-322636 A1 | 11/2003 |
| JP | 2004-108788 A1 | 4/2004 |
| JP | 2004-125482 A1 | 4/2004 |
| JP | 2004-245772 A1 | 9/2004 |
| JP | 2006-284223 | 10/2006 |
| JP | 2009-092431 A1 | 4/2009 |
| JP | 2009-175099 | 8/2009 |
| JP | 2009-236833 | 10/2009 |
| WO | 2008/007706 A1 | 1/2008 |

* cited by examiner

GAS SENSOR

CROSS-REFERENCE TO RELATED APPLICATIONS

This application is a continuation of U.S. application Ser. No. 13/043,888 filed Mar. 9, 2011, the entirety of which is incorporated herein by reference, and claims the benefit under 35 USC §119(a)-(d) of Japanese Application No. 2010-062728 filed Mar. 18, 2010.

FIELD OF THE INVENTION

The present invention relates to a gas sensor including a sensor element and measuring a predetermined gas component in a measurement gas.

BACKGROUND OF THE INVENTION

Conventionally, various measuring apparatuses have been used for recognizing a concentration of a desired gas component in a measurement gas. For example, as a device for measuring a NOx concentration in a measurement gas such as a combustion gas, known is a gas sensor having an electrochemical pumping cell structured by forming a Pt electrode and a Rh electrode on an oxygen-ion conductive solid electrolyte layer, such as a zirconia ($ZrO_2$) layer. In this gas sensor, an electrode protecting layer constituted by a porous body is formed so as to cover a measuring electrode. The electrode protecting layer serves to limit the amount of NOx flowing into the measuring electrode, and also to protect the measuring electrode.

For example, in a known gas sensor, the electrode protecting layer is formed with a sufficient thickness even near end portions of the measuring electrode to thereby effectively prevent occurrence of cracking in the electrode protecting layer and peeling-off of the electrode protecting layer, which may otherwise be caused by a stress generated by repetitive oxidation/reduction of an electrode metal, or the like (for example, see Japanese Patent Application Laid-Open No. 2006-284223).

However, there is the following problem. When the gas sensor as disclosed in Japanese Patent Application Laid-Open No. 2006-284223 is mounted in an exhaust system of an internal combustion engine such as an automobile engine and the internal combustion engine is driven, harmful substances (Mg, Na, Ca, and the like) contained in the exhaust gas may clog the electrode protective layer constituted by the porous body. Such clogging of the electrode protective layer makes it difficult that a measurement gas reaches the measuring electrode, so that the sensitivity of the gas sensor to a measurement gas component such as NOx, in other words, a measurement accuracy, gradually deteriorates along with the use of the gas sensor.

Additionally, in the gas sensor as disclosed in Japanese Patent Application Laid-Open No. 2006-284223, occurrence of cracking or peeling-off of the electrode protective layer is effectively prevented by devising the structure of the electrode protective layer, but a stress is still applied to the electrode protective layer because of repetitive oxidation/reduction of the electrode metal, or the like. That is, the above-described gas sensor involves a problem that the possibility of occurrence of cracking or peeling-off of the electrode protective layer increases along with the use, and the measurement accuracy deteriorates due to the occurrence of cracking, peeling-off, or the like, of the electrode protective layer.

SUMMARY OF THE INVENTION

The present invention is directed to a sensor element included in a gas sensor which measures a predetermined gas component in a measurement gas.

According to the present invention, a gas sensor detecting a predetermined gas component in a measurement gas includes a sensor element constituted by an oxygen-ion conductive solid electrolyte as a main component. The sensor element includes: an internal space to which the measurement gas is introduced; a first electrode formed on a surface of the internal space; a second electrode formed in a space different from the internal space; a pumping cell including the first electrode and the second electrode; a third electrode formed on a surface of the internal space and exposed in the internal space; a fourth electrode formed in a portion different from the internal space; a measuring cell including the third electrode and the fourth electrode; and a porous diffusion layer which applies a predetermined diffusion resistance to the measurement gas. The pumping cell is operable to pump out oxygen existing in the internal space when a predetermined voltage is applied between the first electrode and the second electrode. The porous diffusion layer is buried at a position in the internal space which is nearer to an inlet of the measurement gas than the third electrode is. The third electrode reduces an oxide gas component in the predetermined gas component to which the predetermined diffusion resistance has been applied by the porous diffusion layer. The measuring cell is operable to measure a current which flows between the third electrode and the fourth electrode when a voltage corresponding to the degree of reduction of the oxide gas component in the third electrode is applied between the third electrode and the fourth electrode.

This can realize a gas sensor whose measurement accuracy is stably maintained even through the repetitive use.

Preferably, in the gas sensor according to the present invention, the porous diffusion layer is constituted of a porous body having an average pore diameter of 200 nm or more and 100 µm or less, and a porosity of 20% or more and 80% or less.

This can realize a gas sensor which can apply a predetermined diffusion resistance to the measurement gas without occurrence of clogging of the porous diffusion layer.

Therefore, an object of the present invention is to provide a gas sensor allowing its measurement accuracy to be stably maintained even through the repetitive use.

DETAILED DESCRIPTION OF THE INVENTION

First Preferred Embodiment

Outline Structure of Gas Sensor

Firstly, an outline of the structure of a gas sensor 100 will be described.

Figure 1:
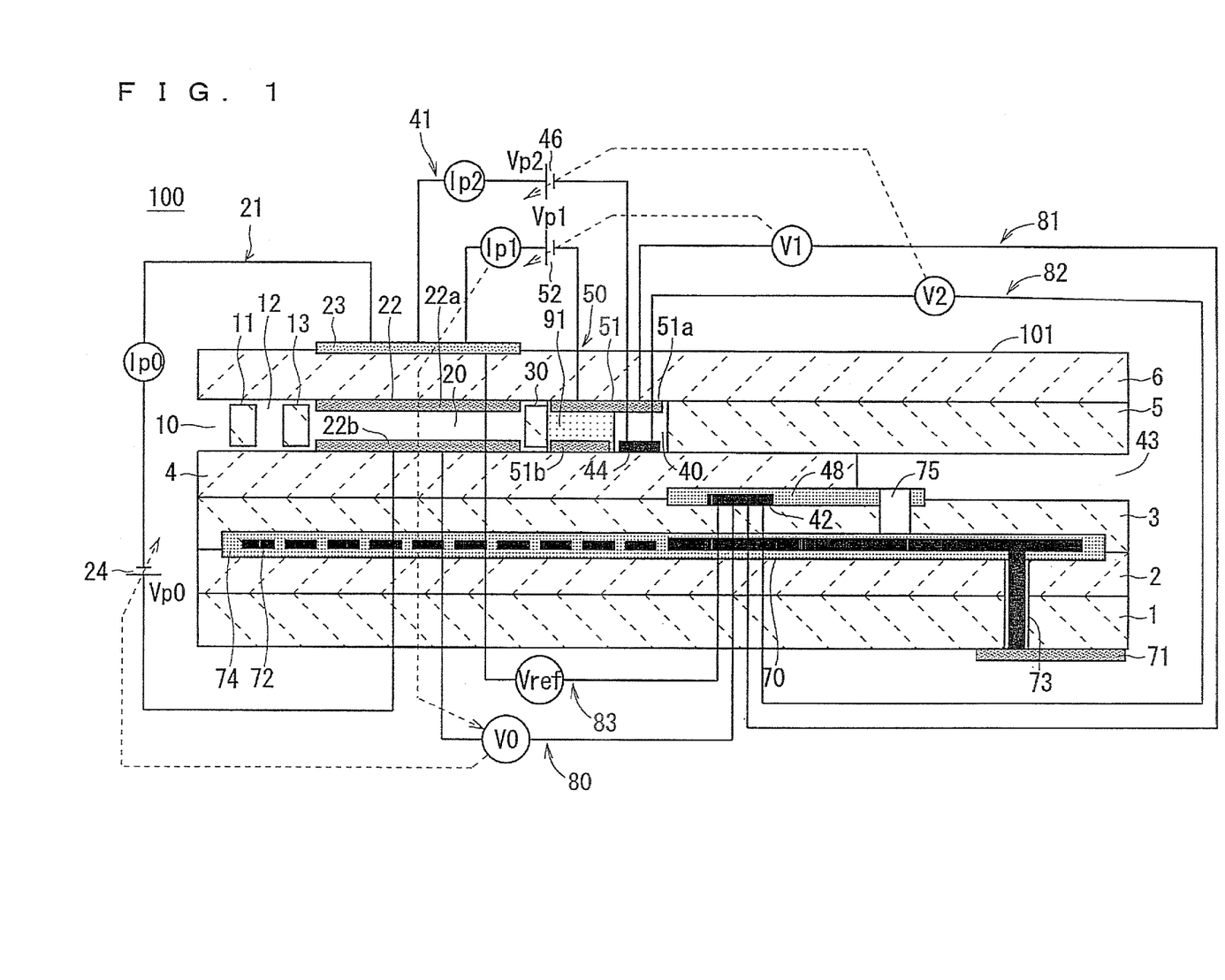
FIG. 1 is a cross-sectional view schematically showing an outline of the structure of a gas sensor according to a first preferred embodiment.

FIG. 1 is a cross-sectional view schematically showing an outline of an exemplified structure of the gas sensor 100. A sensor element 101 is an elongated plate-shaped element having a structure in which six layers, namely, a first substrate layer 1, a second substrate layer 2, a third substrate layer 3, a first solid electrolyte layer 4, a spacer layer 5, and a second solid electrolyte layer 6, are laminated in the mentioned order from the bottom side seen in FIG. 1, each of the layers being formed as an oxygen-ion conductive solid electrolyte layer such as a zirconia ($ZrO_2$) layer. The solid electrolyte forming these six layers is densely airtight. The sensor element 101 is manufactured by, for example, performing a predetermined process and printing a circuit pattern on ceramic green sheets, each of which corresponds to each of the layers, then laminating the green sheets, and furthermore baking the laminated body to integrate it.

Between a lower surface of the second solid electrolyte layer 6 and an upper surface of the first solid electrolyte layer 4 at one end portion of the sensor element 101, a gas inlet 10, a first diffusion control part 11, a buffer space 12, a second diffusion control part 13, a first internal space 20, a third diffusion control part 30, and a second internal space 40 are adjacently formed in the mentioned order so as to be in communication with one another. Here, a first porous diffusion layer 91 is provided in the second internal space 40.

The gas inlet 10, the buffer space 12, the first internal space 20, and the second internal space 40 are spaces within the sensor element 101 provided by hollowing out the spacer layer 5, in which their upper portions are defined by the lower surface of the second solid electrolyte layer 6, their lower portions are defined by the upper surface of the first solid electrolyte layer 4, and their side portions are defined by a side surface of the spacer layer 5.

Each of the first diffusion control part 11, the second diffusion control part 13, and the third diffusion control part 30 is provided as two horizontally long slits (whose openings are elongated in a direction perpendicular to the plane of the drawing sheet of FIG. 1). A part extending from the gas inlet 10 to the second internal space 40 is also referred to as a gas distribution part.

At a position which is farther from the end portion than the gas distribution part is, a reference gas inlet space 43 is provided between an upper surface of the third substrate layer 3 and a lower surface of the spacer layer 5. A side portion of the reference gas inlet space 43 is defined by a side surface of the first solid electrolyte layer 4. As a reference gas for measuring a NOx concentration, for example, air, is introduced into the reference gas inlet space 43.

An air introduction layer 48 is constituted by porous alumina. The reference gas is introduced through the reference gas inlet space 43 into the air introduction layer 48. The air introduction layer 48 is formed so as to cover a reference electrode 42.

The reference electrode 42 is an electrode formed so as to be interposed between the upper surface of the third substrate layer 3 and the first solid electrolyte layer 4. As described above, the air introduction layer 48 leading to the reference gas inlet space 43 is provided around the reference electrode 42. By using the reference electrode 42, an oxygen concentration (oxygen partial pressure) in the first internal space 20 or the second internal space 40 can be measured, as will be described later.

In the gas distribution part, the gas inlet 10 is open to the outside, and a measurement gas is taken into the sensor element 101 from the outside through the gas inlet 10.

The first diffusion control part 11 applies a predetermined diffusion resistance to the measurement gas taken through the gas inlet 10.

The buffer space 12 is provided in order to guide the measurement gas introduced from the first diffusion control part 11, to the second diffusion control part 13.

The second diffusion control part 13 applies a predetermined diffusion resistance to the measurement gas introduced from the buffer space 12 into the first internal space 20.

When the measurement gas is introduced from the outside of the sensor element 101 into the first internal space 20, the measurement gas which was abruptly taken into the sensor element 101 through the gas inlet 10 due to a pressure fluctuation of the measurement gas existing in the outside (a pulsation of exhaust gas pressure, in a case where the measurement gas is an automobile exhaust gas) is not directly introduced into the first internal space 20, but is introduced into the first internal space 20 after a concentration fluctuation in the measurement gas is cancelled through the first diffusion control part 11, the buffer space 12, and the second diffusion control part 13. As a result, the concentration fluctuation in the measurement gas introduced into the first internal space 20 is reduced to as small as negligible.

The first internal space 20 is provided as a space for adjusting oxygen partial pressure in the measurement gas introduced through the second diffusion control part 13. The oxygen partial pressure is adjusted by the operation of a main pumping cell 21.

The main pumping cell 21 is an electrochemical pumping cell constituted by an inside pump electrode 22, an outside pump electrode 23, and a part of the second solid electrolyte layer 6 interposed between these electrodes. The inside pump electrode 22 has a ceiling electrode portion 22a provided on a substantially entire part of the lower surface of the second solid electrolyte layer 6 facing the first internal space 20. The outside pump electrode 23 is provided in a region on an upper surface of the second solid electrolyte layer 6 corresponding to the ceiling electrode portion 22a, so as to be exposed to the outside.

The inside pump electrode 22 is formed over the upper and lower solid electrolyte layers (the second solid electrolyte layer 6 and the first solid electrolyte layer 4) which define the first internal space 20, and the spacer layer 5 which provides a side wall to the first internal space 20. To be specific, the ceiling electrode portion 22a is formed on the lower surface of the second solid electrolyte layer 6 which provides a ceiling surface to the first internal space 20. A bottom electrode portion 22b is formed on the upper surface of the first solid electrolyte layer 4 which provides a bottom surface to the first internal space 20. A side electrode portion (not shown) connecting the ceiling electrode portion 22a to the bottom electrode portion 22b is formed on side wall surfaces (inner surfaces) of the spacer layer 5 which forms both side wall portions of the first internal space 20. Thus, the inside pump electrode 22 has a tunnel-like shape at a location where the side electrode portion is disposed.

Each of the inside pump electrode 22 and the outside pump electrode 23 is formed as a porous cermet electrode (for example, a cermet electrode including Pt containing Au by 1% and zirconia). The inside pump electrode 22 which is brought into contact with the measurement gas is formed using a material having a weakened reduction ability with respect to a NOx component in the measurement gas, or having no reduction ability with respect to the NOx component in the measurement gas.

In the main pumping cell 21, a desired pump voltage Vp0 is applied between the inside pump electrode 22 and the outside pump electrode 23 to make a pump current Ip0 flow in a positive direction or a negative direction between the inside pump electrode 22 and the outside pump electrode 23, and this allows oxygen existing within the first internal space 20 to be pumped out to the outside or oxygen existing in the outside to be pumped into the first internal space 20.

In order to detect an oxygen concentration (oxygen partial pressure) in the atmosphere of the first internal space 20, an electrochemical sensor cell, in other words, a main-pump-controlling oxygen-partial-pressure detection sensor cell 80 is formed with the inside pump electrode 22, the second solid electrolyte 6, the spacer layer 5, the first solid electrolyte 4, the third substrate layer 3, and the reference electrode 42.

The oxygen concentration (oxygen partial pressure) in the first internal space 20 can be recognized by measuring an electromotive force V0 of the main-pump-controlling oxygen-partial-pressure detection sensor cell 80. Moreover, the pump current Ip0 is controlled by feedback-controlling Vp0 so as to maintain the electromotive force V0 constant. Thereby, the oxygen concentration in the first internal space 20 can be maintained at a predetermined constant value.

The third diffusion control part 30 applies a predetermined diffusion resistance to the measurement gas whose oxygen concentration (oxygen partial pressure) has been controlled in the first internal space 20 by the operation of the main pumping cell 21, and guides the measurement gas to the second internal space 40.

The second internal space 40 applies a predetermined diffusion resistance suitable for measurement of a nitrogen oxide (NOx) concentration to the measurement gas introduced through the third diffusion control part 30 by the first porous diffusion layer 91 provided in the second internal space 40, and then supplying the measurement gas to a measuring pumping cell 41.

Figure 2:
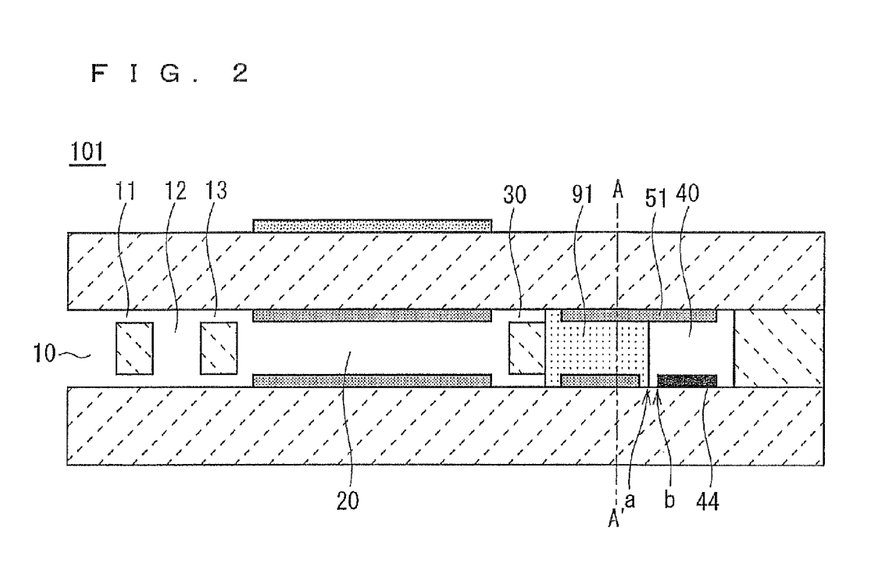
FIG. 2 is a partial cross-sectional view showing an outline of the structure of the gas sensor according to the first preferred embodiment.
Figure 3:
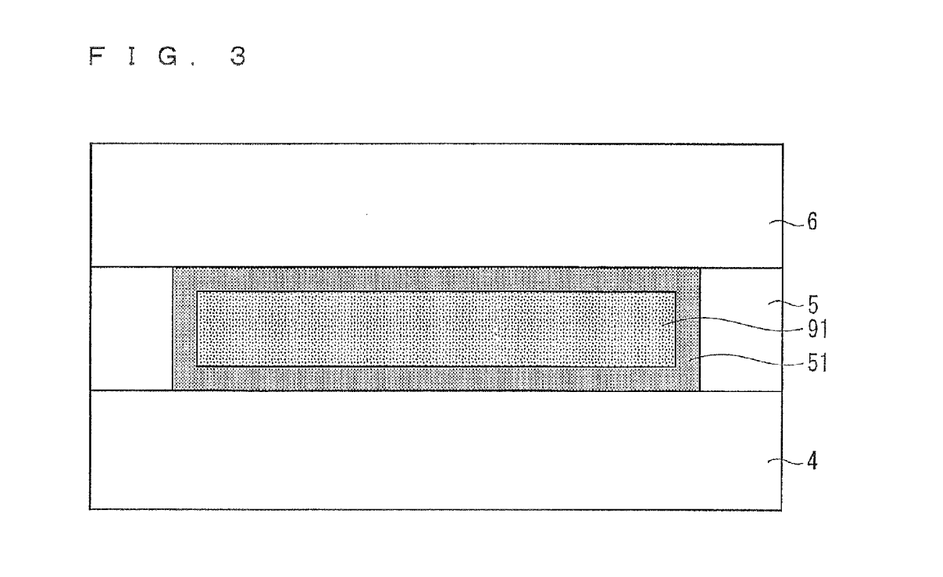
FIG. 3 schematically shows a cross-section of the gas sensor of FIG. 2 taken along the line A-A', as seen from a gas inlet 10 side.

FIG. 2 is a partial cross-sectional view showing an outline of the structure of the sensor element 101 according to this preferred embodiment, for explaining the structure of the second internal space 40. FIG. 3 schematically shows a cross-section of the gas sensor 100 of FIG. 2 taken along the line A-A', as seen from a gas inlet 10 side.

The first porous diffusion layer 91 is constituted by a porous body whose average pore diameter and porosity are greater than at least the solid electrolyte constituting each layer of the sensor element 101. Preferably, first porous diffusion layer 91 is a layer constituted of a porous body containing, as a main component, at least one of metals or ceramics such as alumina, zirconia, and the like.

As shown in FIGS. 2 and 3, the first porous diffusion layer 91 is buried in a space within the second internal space 40 extending from the boundary with the third diffusion control part 30 to a predetermined position a with respect to a lengthwise direction of the sensor element. The position a is located nearer to the gas inlet 10 than an end portion b of a measuring electrode 44 (which will be described later) at the gas inlet 10 side is.

A distance from the boundary with the third diffusion control part 30 to the position a, and the average pore diameter and the porosity of the first porous diffusion layer 91 may be appropriately determined in accordance with the degree of the diffusion resistance suitable for the measurement of the nitrogen oxide (NOx) concentration which is applied to the measurement gas by the first porous diffusion layer 91. The average pore diameter and the porosity of the first porous diffusion layer 91 are calculated by photographing a cross-section of the first porous diffusion layer 91 by a scanning electron microscope (SEM) and extracting a pore portion by an image analysis.

However, it is preferable that the first porous diffusion layer 91 has an average pore diameter of 200 nm to 100 μm and a porosity of 20 to 80%. When the average pore diameter and the porosity are set in these ranges, no clogging occurs in the first porous diffusion layer 91 while sufficiently catching harmful substance particles, and a desired diffusion resistance can be applied to the measurement gas. Here, the harmful substances are not only solid particles suspended in the measurement gas, but also may be in a liquid or gaseous state and contained in the measurement gas. Clogging of the first porous diffusion layer 91 can be caused not only by solid harmful substance particles adhering to a pore surface but also by a progress of deposition of liquid or gaseous harmful substance particles.

If the first porous diffusion layer 91 has an average pore diameter of less than 200 nm or a porosity of less than 20%, harmful substances contained in the measurement gas adhere and clogging occurs in the first porous diffusion layer 91 to make it difficult that the measurement gas reaches the measuring electrode 44, which is not preferable because the measurement performance of the gas sensor 100 deteriorates.

On the other hand, if the first porous diffusion layer 91 has an average pore diameter of more than 100 μm or a porosity of more than 80%, most of the harmful substance particles is not caught and passes through the first porous diffusion layer 91, which is not preferable. The first porous diffusion layer 91 having a porosity of more than 80% also involves the problem that suitable shaping thereof is difficult.

In this manner, in the second internal space 40, the first porous diffusion layer 91 applies a predetermined diffusion resistance suitable for measurement of the nitrogen oxide (NOx) concentration, to the measurement gas introduced through the third diffusion control part 30.

Additionally, in the second internal space 40, an auxiliary pumping cell 50 performs further adjustment of oxygen partial pressure on the measurement gas whose oxygen concentration (oxygen partial pressure) has been adjusted in advance in the first internal space 20 and which has then been introduced through the third diffusion control part 30. This enables an oxygen concentration in the second internal space 40 to be accurately maintained constant. Therefore, the gas sensor 100 can measure a NOx concentration with a high accuracy.

The auxiliary pumping cell 50 is an auxiliary electrochemical pumping cell constituted by an auxiliary pump electrode 51, the outside pump electrode 23 (not limited to the outside pump electrode 23 but may be any appropriate electrode positioned outside the sensor element 101), and the second solid electrolyte layer 6. The auxiliary pump electrode 51 has a ceiling electrode portion 51a provided on a substantially entire part of the lower surface of the second solid electrolyte layer 6 facing the second internal space 40.

Similarly to the inside pump electrode 22 provided in the first internal space 20, the auxiliary pump electrode 51 has a tunnel-like shape and provided in the second internal space 40. That is, the ceiling electrode portion 51a is formed on the second solid electrolyte layer 6 which provides a ceiling surface to the second internal space 40. A bottom electrode portion 51b is formed on the first solid electrolyte layer 4 which provides a bottom surface to the second internal space 40. A side electrode portion (not shown) connecting the ceiling electrode portion 51a to the bottom electrode portion 51b is formed on both wall surfaces of the spacer layer 5 which provides side walls to the second internal space 40.

Similarly to the inside pump electrode 22, the auxiliary pump electrode 51 is formed using a material having a weakened reduction ability with respect to a NOx component in the measurement gas, or having no reduction ability with respect to the NOx component in the measurement gas.

In the auxiliary pumping cell 50, a desired voltage Vp1 is applied between the auxiliary pump electrode 51 and the outside pump electrode 23, and this allows oxygen existing in the atmosphere of the second internal space 40 to be pumped out to the outside or oxygen existing in the outside to be pumped into the second internal space 40.

In order to control oxygen partial pressure in the atmosphere of the second internal space 40, an electrochemical sensor cell, in other words, an auxiliary-pump-controlling oxygen-partial-pressure detection sensor cell 81 is formed with the auxiliary pump electrode 51, the reference electrode 42, the second solid electrolyte layer 6, the spacer layer 5, the first solid electrolyte layer 4, and the third substrate layer 3.

A variable power source 52 causes the auxiliary pumping cell 50 to perform pumping. The variable power source 52 is voltage-controlled based on an electromotive force V1 which is detected by the auxiliary-pump-controlling oxygen-partial-pressure detection sensor cell 81. Therefore, the oxygen partial pressure in the atmosphere of the second internal space 40 is lowered to have substantially no influence on the NOx measurement.

At the same time, a pump current Ip1 of the auxiliary pumping cell 50 is used for a control of the electromotive force of the main-pump-controlling oxygen-partial-pressure detection sensor cell 80. Specifically, the pump current Ip1 is inputted as a control signal to the main-pump-controlling oxygen-partial-pressure detection sensor cell 80, and its electromotive force V0 is controlled, so that a gradient of the oxygen partial pressure in the measurement gas introduced through the third diffusion control part 30 into the second internal space 40 is maintained so as to be always constant. When used as a NOx sensor, the oxygen concentration in the second internal space 40 is maintained at a constant value of approximately 0.001 ppm, by the operations of the main pumping cell 21 and the auxiliary pumping cell 50.

Thus, in the gas sensor 100, by operating the main pumping cell 21 and the auxiliary pumping cell 50, the oxygen partial pressure is always maintained to be a constant low value (value having substantially no influence on the measurement of NOx).

In the second internal space 40, the measurement gas whose oxygen concentration has been adjusted is measured for the NOx concentration by the operation of the measuring pumping cell 41. The measuring pumping cell 41 is an electrochemical pumping cell constituted by the measuring electrode 44, the outside pump electrode 23, the second solid electrolyte layer 6, the spacer layer 5, and the first solid electrolyte layer 4. The measuring electrode 44 is provided at a position on the upper surface of the first solid electrolyte layer 4 facing the second internal space 40, the position being spaced from the first porous diffusion layer 91.

The measuring electrode 44 is a porous cermet electrode having a substantially rectangular shape in a plan view. The measuring electrode 44 also functions as a NOx reducing catalyst which reduces NOx existing in the atmosphere of the second internal space 40.

The measuring pumping cell 41 can pump out oxygen generated by decomposition of nitrogen oxide in the atmosphere around the measuring electrode 44, and detects the amount of the generated oxygen as a pump current Ip2.

In order to detect oxygen partial pressure around the measuring electrode 44, an electrochemical sensor cell, in other words, a measuring-pump-controlling oxygen-partial-pressure detection sensor cell 82 is formed with the second solid electrolyte layer 6, the spacer layer 5, the first solid electrolyte layer 4, the third substrate layer 3, the measuring electrode 44, and the reference electrode 42. The variable power source 46 is controlled based on an electromotive force V2 detected by the measuring-pump-controlling oxygen-partial-pressure detection sensor cell 82.

As described above, the measurement gas introduced into the second internal space 40 reaches the measuring electrode 44 after the predetermined diffusion resistance suitable for measurement of the nitrogen oxide (NOx) concentration is applied thereon by the first porous diffusion layer 91 and additionally the oxygen partial pressure of the measurement gas is controlled by the auxiliary pumping cell 50. Nitrogen oxide having reached the measuring electrode 44 is reduced ($2NO \rightarrow N_2+O_2$), to generate oxygen. The generated oxygen is pumped by the measuring pumping cell 41. At this time, a voltage Vp2 of the variable power source is controlled such that a control voltage V2 detected by the measuring-pump-controlling oxygen-partial-pressure detection sensor cell 82 can be maintained constant. The amount of oxygen generated around the measuring electrode 44 is proportional to a nitrogen-oxide concentration in the measurement gas. Thus, the nitrogen-oxide concentration in the measurement gas is calculated by using the pump current Ip2 of the measuring pumping cell 41.

In other words, in the gas sensor 100, the NOx concentration in the measurement gas can be recognized based on the pump current Ip2 which flows when the oxygen generated by the reduction of NOx is pumped out by the measuring pumping cell 41 substantially in proportion to the NOx concentration in the measurement gas.

If the measuring electrode 44, the first solid electrolyte layer 4, the third substrate layer 3, and the reference electrode 42 are combined to form an electrochemical sensor cell functioning as oxygen-partial-pressure detection means, an electromotive force can be detected in accordance with a difference between the amount of oxygen generated by the reduction of a NOx component in the atmosphere around the measuring electrode 44 and the amount of oxygen contained in a reference atmosphere. Thereby, a concentration of the NOx component in the measurement gas can be obtained.

An electrochemical sensor cell 83 is formed with the second solid electrolyte layer 6, the spacer layer 5, the first solid electrolyte layer 4, the third substrate layer 3, the outside pump electrode 23, and the reference electrode 42. By an electromotive force Vref obtained by the sensor cell 83, oxygen partial pressure in the measurement gas existing in the outside of the sensor can be detected.

Furthermore, in order to enhance an oxygen-ion conductivity of the solid electrolyte, the sensor element 101 includes a heater part 70 serving for a temperature control for heating and keeping warm the sensor element 101. The heater part 70 includes a heater electrode 71, a heater 72, a through hole 73, a heater insulating layer 74, and a pressure diffusion hole 75.

The heater electrode 71 is an electrode formed in contact with a lower surface of the first substrate layer 1. By connecting the heater electrode 71 to an external power source, electrical power can be supplied to the heater part 70 from the outside.

The heater 72 is an electric resistor interposed vertically between the second substrate layer 2 and the third substrate layer 3. The heater 72 is connected to the heater electrode 71 via the through hole 73. The heater 72 generates heat when power is supplied from the outside through the heater electrode 71, and heats and keeps warm the solid electrolyte which forms the sensor element 101.

The heater 72 is buried over the entire area extending from the first internal space 20 to the second internal space 40, so that the temperature of the entire sensor element 101 can be adjusted at a temperature at which the solid electrolyte is activated.

The heater insulating layer 74 is an insulating layer constituted by an insulator such as alumina and formed on upper and lower surfaces of the heater 72. The heater insulating layer 74 is formed for the purpose of providing an electrical insulation between the second substrate layer 2 and the heater 72 and an electrical insulation between the third substrate layer 3 and the heater 72.

The pressure diffusion hole 75 is formed through the third substrate layer 3, and communicates with the reference gas inlet space 43. The pressure diffusion hole 75 is formed for the purpose of relieving a rise in the internal pressure which is involved in a temperature rise in the heater insulating layer 74.

As described above, in the gas sensor 100 according to this preferred embodiment, the first porous diffusion layer 91 is provided instead of the electrode protecting layer which is formed so as to cover the measuring electrode 44 in a conventional gas sensor. Thus, the diffusion resistance of the measurement gas supplied to the measuring electrode 44 is adjusted. Since there is no electrode protecting layer, all of the various problems (such as the problem that harmful substances contained in the measurement gas clog the electrode protecting layer, and the problem that cracking or peeling-off occurs in the electrode protecting layer) of the conventional gas sensor which are caused by the formation of the electrode protecting layer can be removed.

In the gas sensor 100 according to this preferred embodiment, the measurement gas whose oxygen concentration has been adjusted by the auxiliary pumping cell 50 does not reach the measuring electrode 44 via an electrode protective layer, but directly reaches the measuring electrode 44. This may cause harmful substances contained in the measurement gas to directly reach the measuring electrode 44 after passing through the first porous diffusion layer 91.

However, most of the harmful substance particles (particularly solid particles having a relatively large particle diameter) is in advance caught by the first porous diffusion layer 91. Accordingly, very small harmful substance particles are contained in the measurement gas having reached the measuring electrode 44. Therefore, if harmful substance particles contained in the measurement gas reach the measuring electrode 44 and adhere to the measuring electrode 44, there is little influence on the oxidation/reduction of the electrode metal.

Thus, the gas sensor 100 according to this preferred embodiment suitably suppresses a deterioration in the measurement accuracy along with the use, which may otherwise be caused by occurrence of clogging, cracking, and peeling-off of the electrode protecting layer. In other words, the gas sensor 100 according to this preferred embodiment can stably maintain its measurement accuracy even through the repetitive use.

The sensor element 101 including the first porous diffusion layer 91 described above can be formed by, for example, performing a predetermined process on a ceramic green sheet corresponding to the spacer layer 5 in the above-described green-sheet process, then applying to a surface of the first solid electrolyte layer 4 a paste containing a constituent material (such as alumina and silica) of a porous body serving as the first porous diffusion layer 91 and a material (such as powder and particles of methylcellulose, starch, carbon black, theobromine, or the like) for forming pores which will disappear due to baking, and then laminating and baking the ceramic green sheets corresponding to the respective layers in the same manner as described above.

In this manner, according to this preferred embodiment, in the gas sensor 100, the first porous diffusion layer 91 is provided within the second internal space 40, and thereby the measurement accuracy can be stably maintained even through the repetitive use.

Second Preferred Embodiment

In a second preferred embodiment, a description will be given of a case where a porous diffusion layer is provided at a position different from the position in the gas sensor 100 according to the first preferred embodiment.

Figure 4:
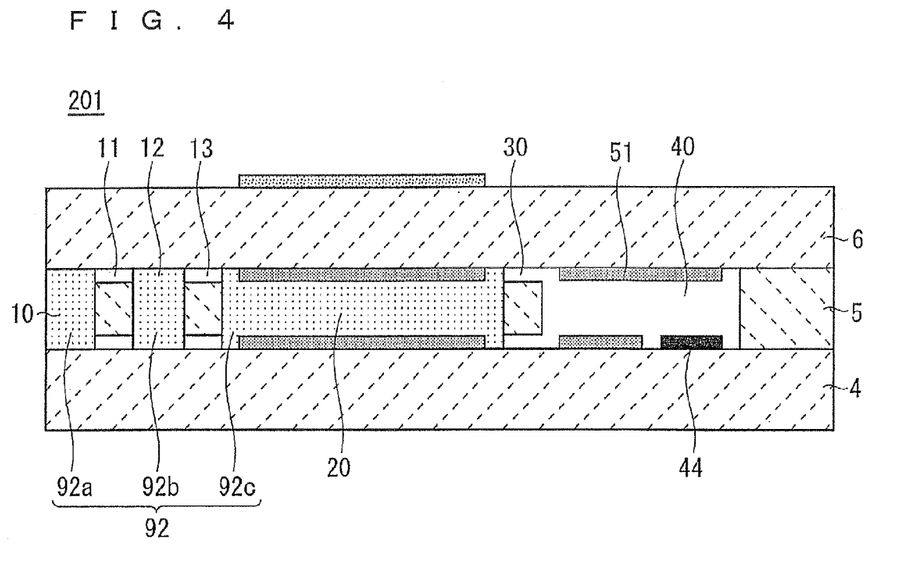
FIG. 4 is a partial cross-sectional view showing an outline of the structure of a gas sensor according to a second preferred embodiment.

FIG. 4 is a partial cross-sectional view showing an outline of the structure of a sensor element 201 of a gas sensor 200 according to the second preferred embodiment. The same parts of the structure as those of the sensor element 101 according to the first preferred embodiment will be denoted by the same corresponding reference numerals, without descriptions thereof.

As shown in FIG. 4, the sensor element 201 has a porous diffusion layer group 92 including a second porous diffusion layer 92a buried in the gas inlet 10, a third porous diffusion layer 92b buried in the buffer space 12, and a fourth porous diffusion layer 92c buried in the first internal space 20. Unlike the first preferred embodiment, the first porous diffusion layer 91 is not provided in the second internal space 40. The measuring electrode 44 is exposed.

Similarly to the first porous diffusion layer 91, each of the three porous diffusion layers included in the porous diffusion layer group 92 is a layer constituted of a porous body having a larger average pore diameter and a larger porosity than those of the solid electrolyte constituting each layer of the sensor element 101, and preferably constituted of a porous body containing, as a main component, at least one of metals or ceramics such as alumina, zirconia, and the like.

The average pore diameter and the porosity of the porous diffusion layer group 92 may be appropriately determined in accordance with the degree of the diffusion resistance suitable for the measurement of the nitrogen oxide (NOx) concentration which is applied to the measurement gas introduced from the outside through the gas inlet 10.

It is preferable that, similarly to the first porous diffusion layer 91, each of the three porous diffusion layers included in the porous diffusion layer group 92 has an average pore diameter of 200 nm to 100 μm and a porosity of 20% to 80%. The average pore diameter and the porosity of each layer are calculated by photographing a cross-section thereof by a scanning electron microscope (SEM) and extracting a pore portion by an image analysis.

In the sensor element 201, the measurement gas introduced from the outside through the gas inlet 10 sequentially passes through the second porous diffusion layer 92a, the first diffusion control part 11, the third porous diffusion layer 92b, the second diffusion control part 13, the fourth porous diffusion layer 92c, and the third diffusion control part 30. Thereby, the measurement gas to which a predetermined diffusion resistance suitable for the measurement of the nitrogen oxide (NOx) concentration is applied is introduced into the second internal space 40 and thus reaches the measuring electrode 44.

That is, in the gas sensor 200 according to this preferred embodiment, instead of the electrode protecting layer formed so as to cover the measuring electrode 44 in the conventional gas sensor, the porous diffusion layer group 92 is provided in the gas inlet 10, the buffer space 12, and the first internal space 20, thereby adjusting the diffusion resistance of the measurement gas supplied to the measuring electrode. Since no electrode protecting layer is provided, all of the various problems of the conventional gas sensor which are caused by the formation of the electrode protecting layer can be removed similarly to the first preferred embodiment.

As described above, according to this preferred embodiment, similarly to the first preferred embodiment, by providing the porous diffusion layer group 92 in the gas sensor 200, the measurement accuracy can be stably maintained even through the repetitive use.

<Modification>

In the description given above, instead of forming the electrode protecting layer so as to cover the measuring electrode 44, the first porous diffusion layer 91 is formed in a region within the second internal space 40, or the second porous diffusion layer 92a, the third porous diffusion layer 92b, and the fourth porous diffusion layer 92c are formed in the gas inlet 10, the buffer space 12, and the first internal space 20, respectively. However, application of the present invention is not limited thereto, and the porous diffusion layer may be formed in any one of the gas inlet 10, the buffer space 12, the first internal space 20, and the second internal space 40 or more.

EXAMPLES

Example 1

In Example 1, an Mg poisoning test was performed on a gas sensor A, a gas sensor B, and a gas sensor C. The gas sensor A is an example of the gas sensor 100 according to the first preferred embodiment. The gas sensor B is an example of the gas sensor 200 according to the second preferred embodiment. The gas sensor C is a comparative example. In the gas sensor A, the first porous diffusion layer 91 has an average pore diameter of 3 μm, and a porosity of 48%. In the gas sensor B, the porous diffusion layer group 92 has an average pore diameter of 12 μm, and a porosity of 32%. The gas sensor C is a conventional gas sensor in which the measuring electrode 44 is covered by an electrode protecting layer constituted of a porous body.

In the Mg poisoning test, an aqueous solution containing ion such as Mg ion was dropped to the vicinity of an end portion of a sensor element and then the gas sensor was driven. This operation was repetitively performed, and a change rate of a sensor output (Ip2) relative to the amount of dropped aqueous solution was measured. The dropped amount was 10 μl in each drop, and the total amount of dropped aqueous solution was 80 μl. In this example, the change rate of the sensor output (Ip2) is a value represented by the ratio of a difference value in the sensor output between when no aqueous solution was dropped (the dropped amount: 0 μl) and when the aqueous solution was dropped, with respect to the sensor output obtained when the aqueous solution was not dropped.

In the Mg poisoning test, when a porous body is clogged due to adhering of Mg or the like, the change rate of the sensor output (Ip2) varies. Therefore, by measuring the change rate of the sensor output (Ip2), whether the porous body is clogged by a substance such as Mg or not can be determined.

Figure 5:
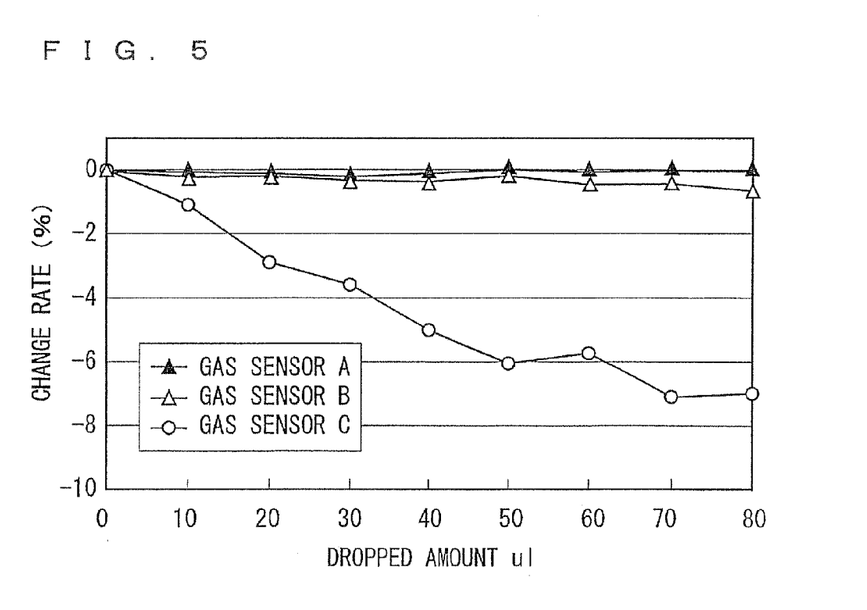
FIG. 5 shows the relationship between the amount of dropped aqueous solution and the change rate of a sensor output.

FIG. 5 shows a result of the Mg poisoning test. As shown in FIG. 5, in the gas sensors A and B, the change rate was maintained at almost 0% irrespective of the dropped amount. In the gas sensor C, on the other hand, the change rate was lowered as the dropped amount increased. From this result, it can be determined that the porous body was clogged only in the gas sensor C. This result indicates that providing the first porous diffusion layer 91 or the porous diffusion layer group 92 instead of the electrode protecting layer as in the gas sensors A and B is effective in suppressing the variation in the change rate of the sensor output (Ip2) which is caused by the clogging of the porous body.

As the amount of dropped aqueous solution increases, a driving time (a time over the repetitive use) of the gas sensor increases. Therefore, it is considered that the result shown in FIG. 5 also shows the relationship between the driving time of the gas sensor and the change rate of the sensor output (Ip2) under a state where adhering of harmful substances such as Mg to the gas sensor may constantly occur. In the result shown in FIG. 5, in the gas sensors A and B, the change rate was almost 0% irrespective of the driving time. This also indicates that, in the gas sensors A and B, the measuring electrode 44 was hardly influenced by poisoning of harmful substances, in addition to occurrence of no clogging in the first porous diffusion layer 91 or the porous diffusion layer group 92. That is, the result shown in FIG. 5 means that providing the first porous diffusion layer 91 or the porous diffusion layer group 92 instead of the electrode protecting layer is effective in suppressing a deterioration in the measurement accuracy which may be caused by the repetitive use.

Example 2

In Example 2, gas sensors D and E as comparative examples were added to the three gas sensors A to C used in Example 1. Thus, an oxidation/reduction test was performed on five gas sensors in total. The structures of the gas sensors D and E are the same as the structure of the gas sensor C which was the comparative example of Example 1.

In the oxidation/reduction test, the atmosphere around the measuring electrode was controlled so as to alternately realize an oxidation atmosphere and a reduction atmosphere, and the change rate of the sensor output (Ip2) relative to the number of repetition of the oxidation/reduction was measured. The oxidation atmosphere was formed by introducing air, and the reduction atmosphere was formed by introducing an inert gas. In this example, the change rate of the sensor output (Ip2) is a value represented by the ratio of a difference value in the sensor output when the oxidation/reduction was performed once and when the oxidation/reduction was repeatedly performed, with respect to the sensor output obtained when the oxidation/reduction was performed once.

In the oxidation/reduction test, when cracking or peeling-off occurs in the porous body, the change rate of the sensor output (Ip2) varies. Accordingly, by measuring the change rate of the sensor output (Ip2), whether or not the measurement accuracy deteriorates along with the repetitive use can be determined, and whether or not cracking or peeling-off is occurring in the porous body can also be determined.

Figure 6:
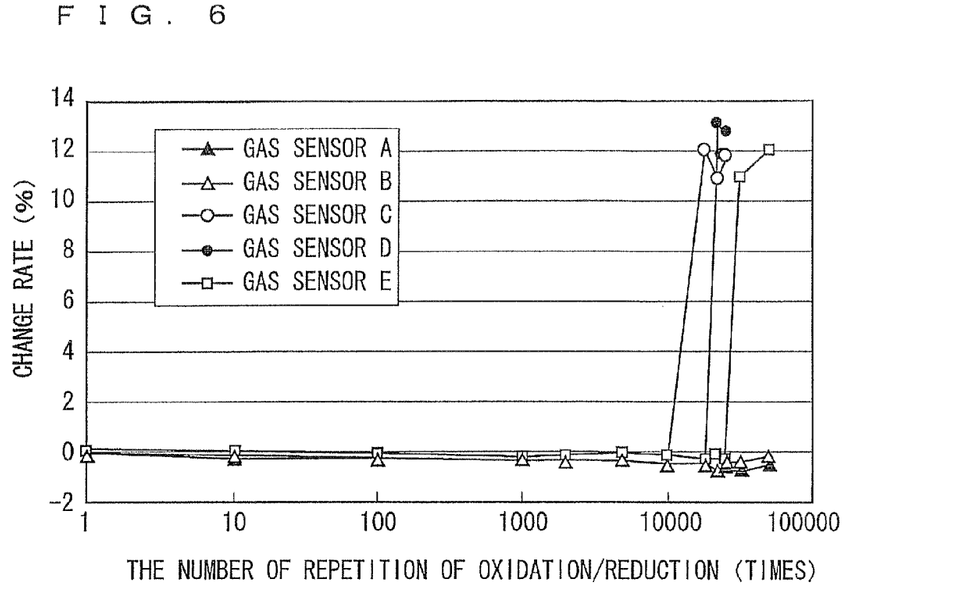
FIG. 6 shows the relationship between the number of repetition of oxidation/reduction and the change rate of the sensor output.

FIG. 6 shows a result of the oxidation/reduction test. As shown in FIG. 6, in the gas sensors A and B, the change rate was maintained at almost 0% irrespective of the number of repetition of the oxidation/reduction. In the gas sensors C to E, when the number of repetition of the oxidation/reduction exceeds 18000 to 32000, the change rate drastically increased. From this results, it can be determined that cracking and/or peeling-off occurred in the porous bodies of the gas sensors C to E. This results means that providing the first porous diffusion layer 91 or the porous diffusion layer group 92 instead of the electrode protecting layer as in the gas sensors A and B is effective in suppressing a deterioration in the measurement accuracy and also effective in suppressing a variation in the change rate of the sensor output (Ip2) which is caused by occurrence of cracking or peeling-off in the porous body.

Example 3

In this example, various gas sensors were prepared, and the Mg poisoning test was performed by the same procedure as that of Example 1. The various gas sensors were prepared by adopting different average porosities and different pore diameters in the first porous diffusion layer 91 of the gas sensor 100 according to the first preferred embodiment.

Figure 7:
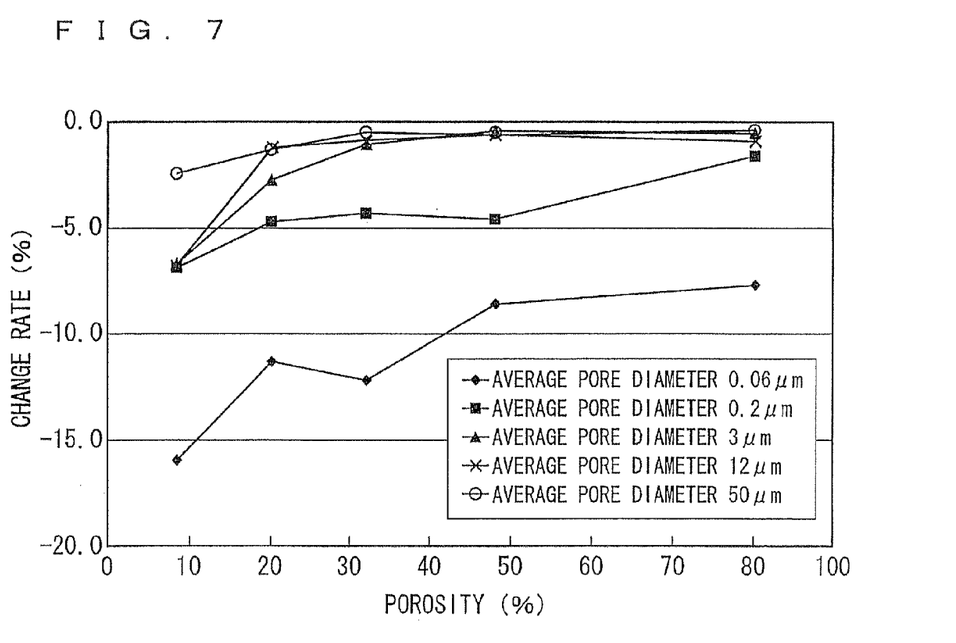
FIG. 7 shows the relationship between the porosity and the sensor output.

FIG. 7 is a graph plotting, against the porosity, the change rate of the sensor output (Ip2) obtained when the amount of dropped aqueous solution containing ion such as Mg ion reached 80 μl, which was obtained in the same calculation method as that of Example 1. It can be considered that there is no problem in practical use when the absolute value of the change rate is equal to or less than 5%. Referring to FIG. 7, it was confirmed that the change rate satisfies this condition when the average pore diameter is equal to or more than 0.2 μm (200 nm) and the porosity is equal to or more than 20%.

What is claimed is:

1. A gas sensor detecting a predetermined gas component in a measurement gas and including a sensor element constituted by an oxygen-ion conductive solid electrolyte as a main component, said sensor element comprising:
    a gas inlet serving as an inlet port of said measurement gas from the outside;
    an internal space to which the measurement gas is introduced from the outside through said gas inlet;
    a first electrode formed on a surface of said internal space;
    a second electrode formed in a space different from said internal space;
    a pumping cell including said first electrode and said second electrode;
    a third electrode formed on a surface of said internal space and exposed in said internal space;
    a fourth electrode formed in a portion different from said internal space;
    a measuring cell including said third electrode and said fourth electrode;
    a plurality of diffusion control parts each of which is provided as one or more slits between said gas inlet and said third electrode; and
    a porous diffusion layer which applies a predetermined diffusion resistance to said measurement gas,
    wherein
    said pumping cell is operable to pump out oxygen existing in said internal space when a predetermined voltage is applied between said first electrode and said second electrode,
    said porous diffusion layer is buried at a position between said third electrode and the nearest of said plurality of diffusion control parts to said third electrode in said internal space,
    said third electrode reduces an oxide gas component in said predetermined gas component to which said predetermined diffusion resistance has been applied by said porous diffusion layer,
    said measuring cell is operable to measure a current which flows between said third electrode and said fourth electrode when a voltage corresponding to the degree of reduction of said oxide gas component in said third electrode is applied between said third electrode and said fourth electrode,
    wherein said porous diffusion layer is spaced from said third electrode.

2. The gas sensor according to claim 1, wherein said porous diffusion layer is constituted of a porous body having an average pore diameter of 200 nm or more and 100 μm or less, and a porosity of 20% or more and 80% or less.

3. The gas sensor according to claim 1, wherein said second electrode and said fourth electrode are shared with a sensor cell for detecting an oxygen partial pressure of the measurement gas outside of the gas sensor.

4. The gas sensor according to claim 1, further comprising:
    a buffer space communicating with said gas inlet under a predetermined diffusion resistance,
    wherein
    said internal space includes a first internal space and a second internal space,
    said pumping cell comprises a main pumping cell and an auxiliary pumping cell,
    said first internal space communicates with said buffer space under a predetermined diffusion resistance,
    said second internal space communicates with said first internal space under a predetermined diffusion resistance,
    said main pumping cell has said first electrode provided in said first internal space,
    said auxiliary pumping cell has said first electrode provided in said second internal space,
    said third electrode is formed on a surface of said second internal space in an exposed manner,
    said porous diffusion layer is buried at a position in said second internal space which is nearer to said gas inlet than said third electrode is.

5. The gas sensor according to claim 4, wherein in said second internal space, said porous diffusion layer is buried in a predetermined range from an end portion of said second internal space at a said gas inlet side with respect to a lengthwise direction of said sensor element.

6. A gas sensor detecting a predetermined gas component in a measurement gas and including a sensor element constituted by an oxygen-ion conductive solid electrolyte as a main component, said sensor element comprising:
    a gas inlet serving as an inlet port of said measurement gas from the outside;
    an internal space to which the measurement gas is introduced from the outside through said gas inlet;
    a first electrode formed on a surface of said internal space;
    a second electrode formed in a space different from said internal space;
    a pumping cell including said first electrode and said second electrode;
    a third electrode formed on a surface of said internal space and exposed in said internal space;
    a fourth electrode formed in a portion different from said internal space;
    a measuring cell including said third electrode and said fourth electrode;
    a plurality of diffusion control parts each of which is provided as one or more slits between said gas inlet and said third electrode;

a porous diffusion layer which applies a predetermined diffusion resistance to said measurement gas, and a buffer space communicating with said gas inlet under a predetermined diffusion resistance, wherein said pumping cell is operable to pump out oxygen existing in said internal space when a predetermined voltage is applied between said first electrode and said second electrode, said third electrode reduces an oxide gas component in said predetermined gas component to which said predetermined diffusion resistance has been applied by said porous diffusion layer, said measuring cell is operable to measure a current which flows between said third electrode and said fourth electrode when a voltage corresponding to the degree of reduction of said oxide gas component in said third electrode is applied between said third electrode and said fourth electrode, said internal space includes a first internal space and a second internal space, said pumping cell comprises a main pumping cell and an auxiliary pumping cell, said first internal space communicates with said buffer space under a predetermined diffusion resistance, said second internal space communicates with said first internal space under a predetermined diffusion resistance, said main pumping cell has said first electrode provided in said first internal space, said auxiliary pumping cell has said first electrode provided in said second internal space, said third electrode is formed on a surface of said second internal space in an exposed manner, and said porous diffusion layer is buried in said first internal space and also buried in said gas inlet and said buffer space.

* * * * *